(12) United States Patent
Saleh et al.

(10) Patent No.: US 10,497,541 B2
(45) Date of Patent: Dec. 3, 2019

(54) APPARATUS AND METHOD FOR PROGRAMMABLE SPATIALLY SELECTIVE NANOSCALE SURFACE FUNCTIONALIZATION

(71) Applicants: Nedal Saleh, Woodbridge, CT (US); Waqas Khalid, Woodbridge, CT (US); Faisal Saleh, Woodbridge, CT (US)

(72) Inventors: Nedal Saleh, Woodbridge, CT (US); Waqas Khalid, Woodbridge, CT (US); Faisal Saleh, Woodbridge, CT (US)

(*) Notice: Subject to any disclaimer, the term of this patent is extended or adjusted under 35 U.S.C. 154(b) by 0 days.

(21) Appl. No.: 15/600,470

(22) Filed: May 19, 2017

(65) Prior Publication Data
US 2017/0338079 A1 Nov. 23, 2017

Related U.S. Application Data

(60) Provisional application No. 62/338,955, filed on May 19, 2016, provisional application No. 62/338,996, filed on May 19, 2016, provisional application No. 62/339,002, filed on May 19, 2016, provisional application No. 62/339,008, filed on May 19, 2016.

(51) Int. Cl.
  *H01J 37/32* (2006.01)
  *B01F 13/00* (2006.01)
  (Continued)

(52) U.S. Cl.
  CPC ...... *H01J 37/3233* (2013.01); *B01F 13/0064* (2013.01); *B01J 19/0093* (2013.01);
  (Continued)

(58) Field of Classification Search
  None
  See application file for complete search history.

(56) References Cited

U.S. PATENT DOCUMENTS 4,509,451 A   4/1985   Collins et al.
5,070,282 A   12/1991  Epsztein
(Continued)

FOREIGN PATENT DOCUMENTS

WO   2010146153 A1   12/2010
WO   2012154306 A1   11/2012
(Continued)

OTHER PUBLICATIONS

3D Nanoprototyping with a DualBeam, www.fei.com/documents/3d-nanoprototyping-with-a-dualbeam, 2013, pp. 1 to 12.
(Continued)

*Primary Examiner* — Shamim Ahmed
(74) *Attorney, Agent, or Firm* — Pillsbury Winthrop Shaw Pittman LLP

(57) ABSTRACT

A spatially selective surface functionalization device configured to generate a pattern of micro plasmas and functionalize a substrate surface may include: a pattern management system, a patterning head, and a gas delivery system, wherein the gas delivery system provides a primed gas mixture for forming a plasma between the patterning head and a target substrate below the patterning head. A patterning head may generate a distribution of micro plasmas from individual directed beams of electrons with spatial separation. A pattern management system may store and manipulate information about a pattern of surface functionalization and generate instructions for regulating a distribution of micro plasmas that functionalize a substrate surface.

21 Claims, 10 Drawing Sheets

(51) Int. Cl.
*B01L 3/00* (2006.01)
*B01J 19/00* (2006.01)
*C12Q 1/6837* (2018.01)
*G01N 1/38* (2006.01)

(52) U.S. Cl.
CPC .......... *B01L 3/5023* (2013.01); *B01L 3/5027* (2013.01); *B01L 3/502715* (2013.01); *B01L 3/502753* (2013.01); *C12Q 1/6837* (2013.01); *H01J 37/3244* (2013.01); *H01J 37/3299* (2013.01); *H01J 37/32366* (2013.01); *H01J 37/32733* (2013.01); *B01J 2219/00781* (2013.01); *B01J 2219/00869* (2013.01); *B01L 2200/06* (2013.01); *B01L 2300/0645* (2013.01); *B01L 2300/0654* (2013.01); *B01L 2300/0681* (2013.01); *B01L 2300/1827* (2013.01); *B01L 2400/0688* (2013.01); *G01N 1/38* (2013.01); *H01J 2237/327* (2013.01); *H01J 2237/334* (2013.01)

(56) References Cited

U.S. PATENT DOCUMENTS

| | | | |
|---|---|---|---|
| 5,294,465 A | | 3/1994 | Gallagher |
| 5,587,586 A | * | 12/1996 | Kruit ...................... H01J 3/021 250/423 F |
| 6,787,122 B2 | | 9/2004 | Zhou |
| 7,220,971 B1 | | 5/2007 | Chang et al. |
| 7,791,055 B2 | | 9/2010 | Williamson et al. |
| 2002/0187556 A1 | | 12/2002 | Shartle et al. |
| 2003/0038244 A1 | | 2/2003 | Thomas et al. |
| 2003/0052096 A1 | | 3/2003 | Crowe et al. |
| 2004/0091399 A1 | | 5/2004 | Chung et al. |
| 2004/0115831 A1 | | 6/2004 | Meathrel et al. |
| 2004/0262540 A1 | | 12/2004 | Nagaseki et al. |
| 2006/0103035 A1 | | 5/2006 | Maruyama |
| 2006/0208649 A1 | | 9/2006 | Rueger et al. |
| 2008/0067421 A1 | | 3/2008 | Cheng et al. |
| 2008/0212216 A1 | | 9/2008 | Milosevic et al. |
| 2008/0283767 A1 | | 11/2008 | Platzgummer |
| 2008/0318334 A1 | | 12/2008 | Robotti |
| 2009/0044875 A1 | | 2/2009 | Griss et al. |
| 2009/0281650 A1 | | 11/2009 | Kassab |
| 2010/0105577 A1 | | 4/2010 | Dugan et al. |
| 2010/0200094 A1 | | 8/2010 | Ermakov |
| 2012/0003394 A1 | | 1/2012 | Mulders et al. |
| 2012/0045863 A1 | | 2/2012 | Hopwood |
| 2012/0123686 A1 | | 5/2012 | Xiang et al. |
| 2013/0098551 A1 | | 4/2013 | Dorf et al. |
| 2013/0206720 A1 | | 8/2013 | Blom et al. |
| 2014/0303037 A1 | * | 10/2014 | Short ............... G01N 33/54306 506/14 |
| 2014/0377146 A1 | | 12/2014 | Putnam et al. |
| 2015/0290669 A1 | | 10/2015 | Li et al. |
| 2016/0299103 A1 | | 10/2016 | Saleh et al. |
| 2017/0098557 A1 | | 4/2017 | Shimizu et al. |
| 2017/0307601 A1 | | 10/2017 | Putnam et al. |
| 2017/0365438 A1 | * | 12/2017 | Akinwande ............. G01L 21/34 |

FOREIGN PATENT DOCUMENTS

| | | |
|---|---|---|
| WO | 2015/051175 A2 | 4/2015 |
| WO | 2015137364 A1 | 9/2015 |
| WO | 2017201505 A3 | 11/2017 |

OTHER PUBLICATIONS

A rapid, inexpensive surface treatment for enhanced functionality of polydimethylsiloxane microfluidic channels, www.ncbi.nlm.nih.gov/pmc/articles/PMC3423308, Jul. 30, 2012, pp. 1 to 12.
Electron beam-induced deposition, Wikipedia, https://en.wikipedia.org/wiki/Electron_beam-induced_deposition, Feb. 20, 2016, pp. 1 to 5.
Electron-beam-induced deposition with carbon nanotube emitters, www.egr.msu.edu/~ldong/Publication/JP200203_APL_81_1919_Dong.pdf, Applied Physics Letters vol. 81, No. 10, Sep. 2, 2002, pp. 1 to 3.
Fabrication and characterization of nanostructures on insulator substrates by electron-beam-induced deposition, IIOP Publishing, Sci. Technol. Adv. Mater. 9 (2008) 023002 (10pp), http://www.tandfonline.com/doi/full/10.1088 /1468-6996/9/2/023002, Aug. 1, 2008, pp. 1 to 11.
Fabrication and Functionalization of Nanochannels by Electron-Beam-Induced Silicon Oxide Deposition, http://pubs.acs.org/doi/abs/10.1021/Ia061321c, Sep. 6, 2006, pp. 1 to 4.
Hydrophilic Surface Modification of PDMS Microchannel for O/W and W/O/W Emulsions, www.mdpi.com/journal/micromachines, Sep. 29, 2015, pp. 1 to 14.
Integration of microplasma and microfluidic technologies for localised microchannel surface modification, Proceedings vol. 8204, SPIE Smart Nano, Micro Materials and Devices, Dec. 4-7, 2011, pp. 1 to 7.
Ion-Enhanced Field Emission for Control of Atmospheric Pressure Discharges, Aerospace and Mechanical Engineering Chemical and Biomolecular Engineering University of Notre Dame, http://www.nd.edu/~sst, Jun. 25, 2014, pp. 1 to 28.
Microfluidics Meets MEMS, Proceedings of the IEEE, vol. 91, No. 6, Jun. 2003, www-mtl.mit.edu/researchgroups/mems-salon/Hongwei_microfluidicMEMS.pdf, Apr. 4, 2003, pp. 1 to 24.
Microplasma, Wikipedia, https://en.wikipedia.org/wiki/Microplasma, Oct. 22, 2015, pp. 1 to 10.
Microplasma-Based Treatment of Inner Surfaces in Microfluidic Devices,www.altmetric.com/details.php?domain=onlinelibrary.wiley.com&doi=10.1002%2Fctpp.200710008, Feb. 1, 2007, pp. 1 to 3.
Multibeam Electron Source using MEMS Electron Optical Components, Journal of Physics: Conference Series 34, International MEMS Conference 2006, http://iopscience.iop.org/article/10.1088/1742-6596/34/1/180/pdf, pp. 1 to 6.
Nanofabrication by advanced electron microscopy using intense and focused beam, IOP Publishing, Sci. Technol. Adv. Mater. 9 (2008) 014110 (20pp), http://iopscience.iop.org/article/10.1088/1468-6996/9/1/014110/meta, May 27, 2008, pp. 1 to 21.
Oxygen plasma treatment for reducing hydrophobicity of a sealed polydimethylsiloxane microchannel, http://www.ncbi.nlm.nih.gov/pmc/articles/PMC2967237/, Sep. 30, 2010, pp. 1 to 8.
Parallel electron-beam-induced deposition using a multi-beam scanning electron microscope, J. Vac. Sci. Technol. B, vol. 29, No. 6, Nov./Dec. 2011, http://avs.scitation.org/doi/abs/10.1116/1.3656027, Oct. 26, 2011, pp. 1 to 4.
Review article: Fabrication of nanofluidic devices, Biomicrofluidics 7, 026501 (2013), American Institute of Physics, http://dx.doi.org/10.1063/1.4794973, Mar. 13, 2013, pp. 1 to 41.
Surface patterning of bonded microfluidic channels, Biomicrofluidics. Sep. 2010; 4(3): 032206, American Institute of Physics, http://dx.doi.org/10.1063/1.3493643, Sep. 30, 2010, pp. 1 to 14.
Surface Technology with Cold Microplasmas, Plasma Processes and Polymers, vol. 4, Issue 3, Apr. 23, 2007, http://onlinelibrary.wiley.com/doi/10.1002/ppap.200600116/full, pp. 1 to 5.
Surface-Tension-Confined Microfluidics and Their Applications, ChemPhysChem 2013, https://www.researchgate.net/publication/234099281, Feb. 2013, pp. 1 to 12.
What is the difference between SEM and FESEM?, ResearchGate, www.researchgate.net/post/What_is_the_difference_between_SEM_and_FESEM, Dec. 20, 2013, pp. 1 to 5.
Micro Systems and Devices for (Bio)chemical Processes, https://books.google.com/books?id=bt3Sd8H0XXAC, Academic Press as in imprint of Elsevier, 2010, pp. 1 to 1.
Related PCT Application No. US2017/033695 filed on May 19, 2017, pp. 1 to 48.
International Search Report and Written Opinion for Related PCT Application No. PCT/US2017/033695 dated Nov. 29, 2017, pp. 1 to 25.
Related U.S. Appl. No. 15/630,095, filed Jun. 22, 2017, pp. 1 to 48.
Restriction Requirement for Related U.S. Appl. No. 15/630,095 dated Sep. 1, 2017, pp. 1 to 10.

(56) References Cited

OTHER PUBLICATIONS

Non-Final Office Action for Related U.S. Appl. No. 15/630,095 dated Dec. 29, 2017, pp. 1 to 26.
Final Office Action for Related U.S. Appl. No. 15/630,095 dated May 3, 2018, pp. 1 to 65.
Related U.S. Appl. No. 15/600,492, filed May 19, 2017, pp. 1 to 48.
Non-Final Office Action for Related U.S. Appl. No. 15/600,492 dated Nov. 1, 2017, pp. 1 to 27.
Restriction Requirement for Related U.S. Appl. No. 15/600,492 dated Jun. 15, 2018, pp. 1 to 6.
Related U.S. Appl. No. 15/630,137, filed Jun. 22, 2017, pp. 1 to 48.
Restriction Requirement for Related U.S. Appl. No. 15/630,137 dated Aug. 2, 2017, pp. 1 to 9.
Non-Final Office Action for Related U.S. Appl. No. 15/630,137 dated Oct. 31, 2017, pp. 1 to 18.
Final Office Action for Related U.S. Appl. No. 15/630,137 dated May 14, 2018, pp. 1 to 17.
Related U.S. Appl. No. 15/600,606, filed May 19, 2017, pp. 1 to 48.
Non-Final Office Action for Related U.S. Appl. No. 15/600,606 dated Aug. 15, 2017, pp. 1 to 8.
Final Office Action for Related U.S. Appl. No. 15/600,606 dated Mar. 16, 2018, pp. 1 to 20.
Related U.S. Appl. No. 15/630,164, filed Jun. 22, 2017, pp. 1 to 48.
Non-Final Office Action for Related U.S. Appl. No. 15/630,164 dated Aug. 14, 2017, pp. 1 to 10.
Noblitt, S.D. et al. Integrated Membrane Filters for Minimizing Hydrodynamic Flow and Filtering in Microfluidic Devices, 2007, Analytical Chemistry, vol. 79(16), pp. 6249-6254.
Final Office Action for Related U.S. Appl. No. 15/630,164 dated Dec. 18, 2017, pp. 1 to 10.
Tachibana, H. et al. Self-propelled continuous-flow PCR in capillary-driven microfluidic device: Microfluidic behavior and DNA amplification, 2015, Sensors and Actuators B vol. 206, pp. 303-310.
Zhu, Y. et al., 'Capillary flow in microchannels', 2010, Microfluid Nanofluid, vol. 8, pp. 275-282.
Non-Final Office Action for Related U.S. Appl. No. 15/630,164 dated Aug. 28, 2018, pp. 1 to 10.
Final Office Action for Related US Patent Application , dated Mar. 13, 2019, pp. 1 to 37.
Khademhosseini, A. et al., "A Soft Lithographic Approach to Fabricate Patterned Microfluidic Channels, Analytical Chemistry," vol. 76, 2004, pp. 3675-3681.
Non-Final Office Action for Related U.S. Appl. No. 15/600,492 dated Sep. 27, 2019, pp. 1 to 14.

* cited by examiner

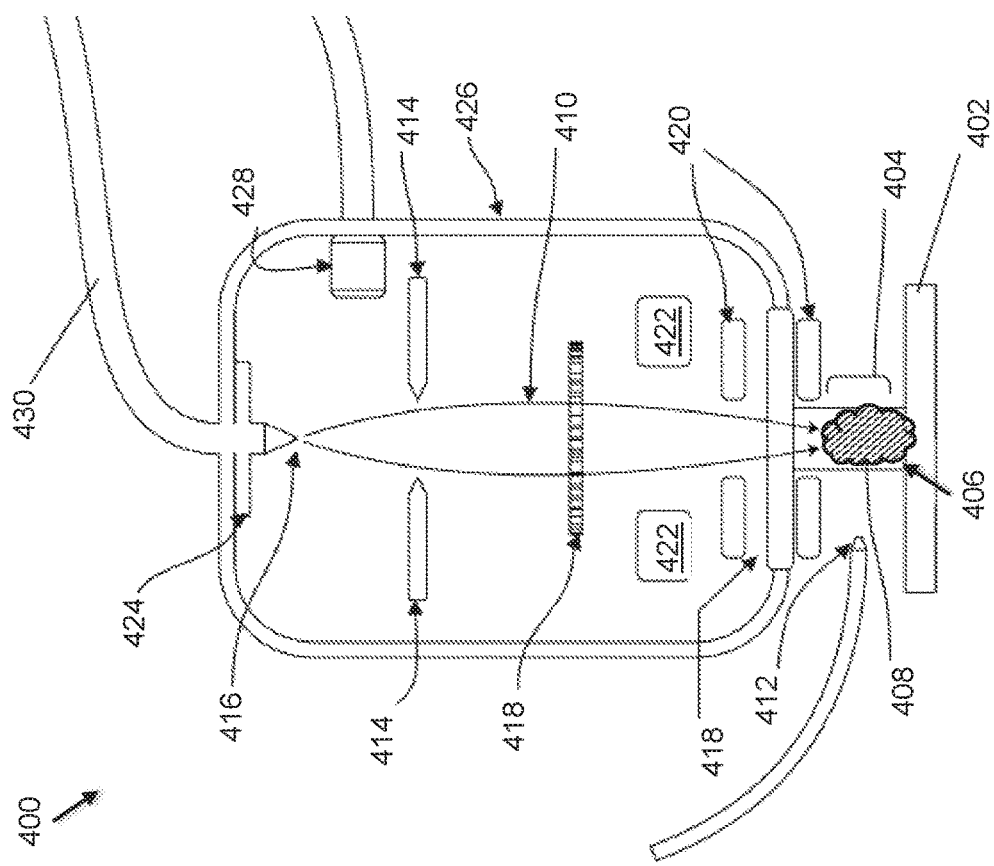

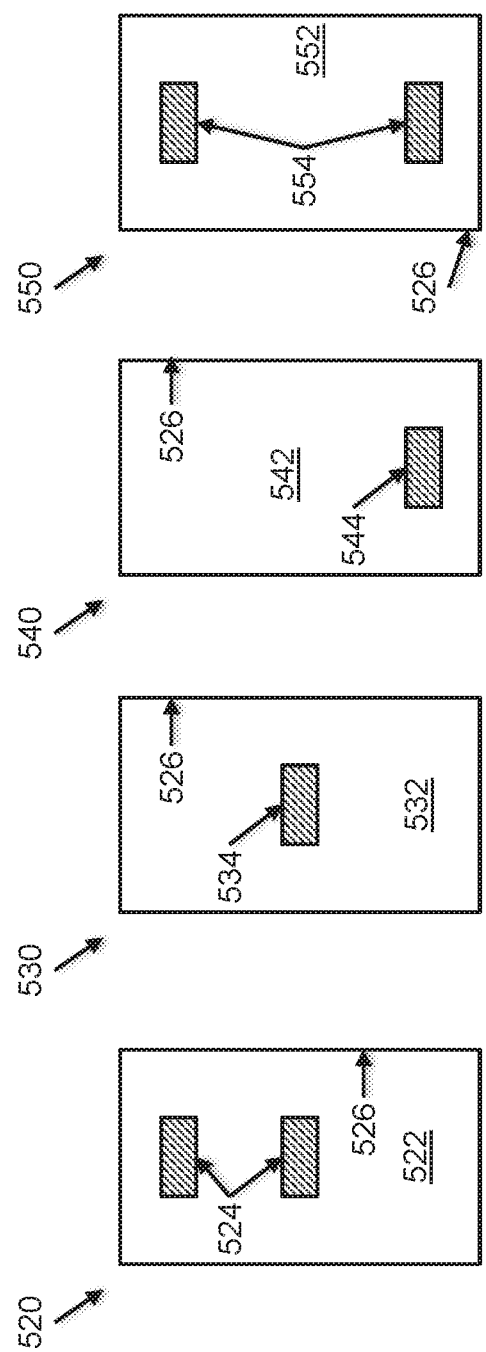

APPARATUS AND METHOD FOR PROGRAMMABLE SPATIALLY SELECTIVE NANOSCALE SURFACE FUNCTIONALIZATION

CROSS-REFERENCE TO RELATED APPLICATIONS

The present patent filing claims the benefit of U.S. Provisional Patent Application 62/338,955, titled APPARATUS AND METHOD FOR PROGRAMMABLE SPATIALLY SELECTIVE NANOSCALE SURFACE FUNCTIONALIZATION, filed 19 May 2016; U.S. Provisional Patent Application 62/338,996, titled PUMP-FREE MICROFLUIDIC ANALYTICAL CHIP, filed 19 May 2016; U.S. Provisional Patent Application 62/339,002, titled PUMP-FREE MICROFLUIDIC ANALYTICAL SYSTEMS, filed 19 May 2016; and U.S. Provisional Patent Application 62/339,008, titled STAND ALONE PUMP-FREE MICROFLUIDIC ANALYTICAL CHIP DEVICE, filed 19 May 2016. The content of each of these earlier filed patent applications is hereby incorporated by reference in its entirety.

FIELD OF THE INVENTION

The invention relates generally to methods and apparatus for performing modification of surfaces of materials. Modification of surfaces may include modifying form and structure of surfaces and modifying the chemical composition of surfaces. Surface modification may be performed using a plasma.

BACKGROUND OF THE INVENTION

The present disclosure relates to a device for forming a plasma to modify surface chemistry or functionalization of a material after exposure of the material to the plasma. Surface chemistry modification may include modifying the hydrophobicity of a surface, modifying a dimension of the surface, modifying an electrochemical characteristic of a material, modifying an optical characteristic of a material, or modifying a dimension of modified area of a surface.

SUMMARY OF THE INVENTION

The invention addressing these and other drawbacks relates to methods, apparatuses, and/or systems for prioritizing retrieval and/or processing of data over retrieval and/or processing of other data.

Aspects of the present disclosure relate to a device for spatially selective surface functionalization, comprising a pattern management system, a patterning head, and a gas delivery system, wherein the patterning head is configured to generate a first distribution of micro plasmas against a top surface of a substrate in a gas mixture at least partially provided by the gas delivery system. The distribution of micro plasmas may be according to a pattern stored in the pattern management system, according to a first portion of the pattern.

Aspects of the present disclosure relate to a method for modifying a surface with a plasma. The method includes operations of energizing a first set of individually addressable electron emission structures in an electron source, the electron source having a membrane with a first surface and a second surface; and creating a blend of gases in a working volume adjacent to the second surface of the membrane on an outer surface of the electron source. The method also includes operations of accelerating electrons from the first set of individually addressable electron emission structures towards the membrane, forming a first set of micro plasmas where the accelerated electrons from the first set of individually addressable electron emission structures intersects the blend of gases, and adjusting a distance between a substrate and the second surface such that the first set of micro plasmas intersects a top surface of the substrate at a first location.

Aspects of the present disclosure relate to a method of making a plasma device having an electron source that comprises operations of forming, in the electron source, an array of individually addressable electron emission structures on an chip, placing, in the electron source, an electron accelerating structure between the chip and a target substrate, and interconnecting the array of individually addressable electron emission structures with a power supply and the electron accelerating structure. The method also includes operations of placing, in a wall of the electron source, a membrane configured to pass a directed beam of electrons, positioning a nozzle of a gas delivery system to deliver a flow of gas into a working volume between the electron source and the target substrate, and connecting a controller element to the power supply configured to regulate an electrical potential between the array of individually addressable electron emission structures and the electron accelerating structure.

These and other features of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise. In addition, as used in the specification and the claims, the term "or" means "and/or" unless the context clearly dictates otherwise. Further, the terms "on", "over", "above", "below", "beneath", and "under" may generally be used to indicate the position of portions of embodiments described herein along an axis through the portions, without an absolute reference to a particular direction. Thus, one portion may be "on" or "above" or "below" or "under" another, even when the portions are rotated with respect to an external frame of reference.

BRIEF DESCRIPTION OF THE DRAWINGS

The invention is illustrated by way of example, and not by way of limitation, in the figures of the accompanying drawing and in which like reference numerals refer to similar elements.

FIG. 4 depicts a cross-sectional analysis of an embodiment of an apparatus having electron emission structures;

FIGS. 5B-5E depict patterns of micro-plasmas generated by a electron-emission patterning head to form the embodiment of FIG. 5A;

Figure 1:
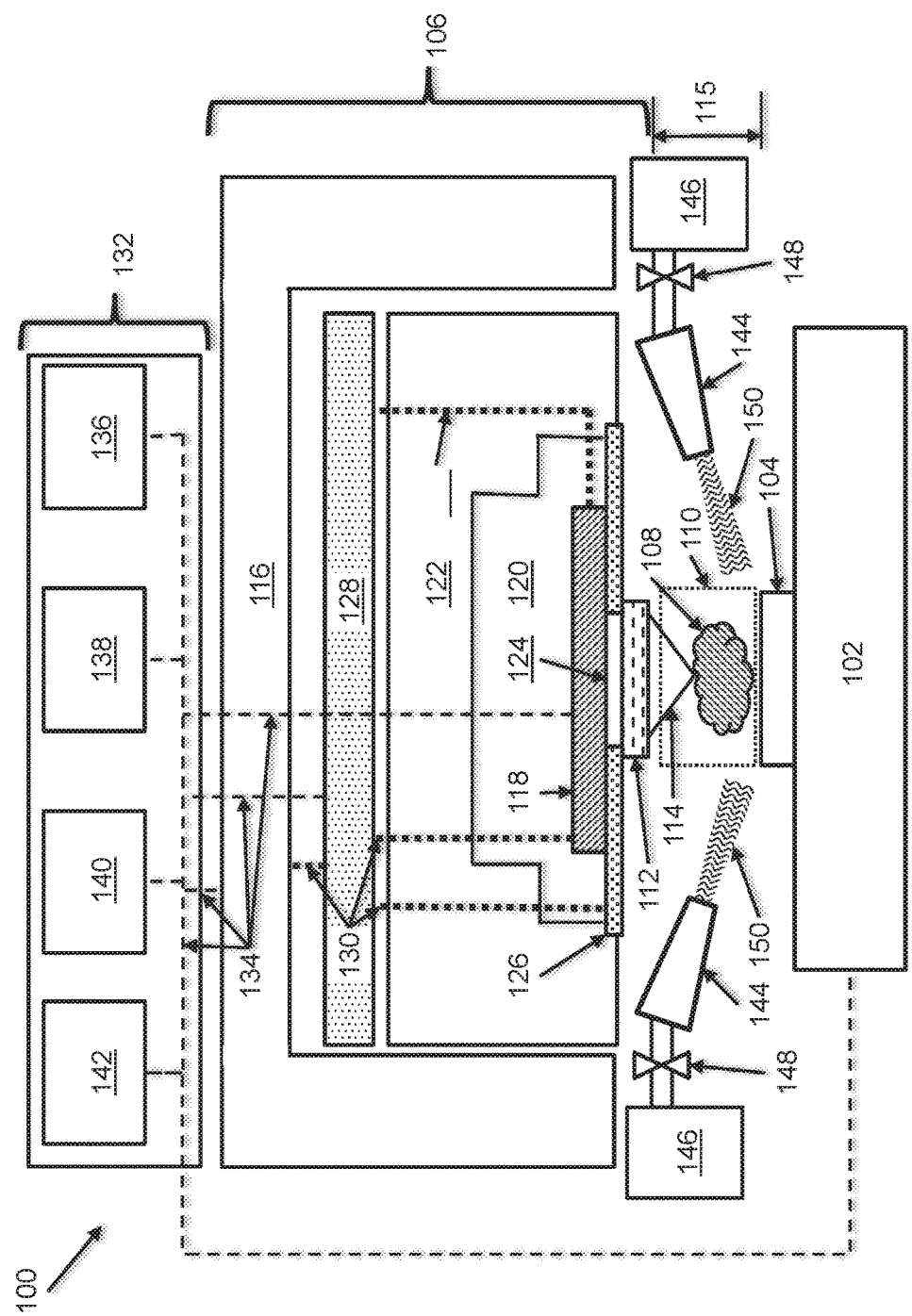
FIG. 1 depicts a cross-sectional diagram of an embodiment of a nanoscale surface functionalization device.

Methods, embodiments, implementations, and apparatus described herein are merely representative of the invention claimed herein. Accordingly, other methods, embodiments, implementations, and apparatus may also fall within the scope of the present disclosure after being envisioned by a person of ordinary skill in the art.

DETAILED DESCRIPTION OF THE INVENTION

Surface modification during a manufacturing processes can impart new properties to materials. One method of surface modification includes using a plasma to modify a chemical structure of the surface. Surface modification using plasma tools can provide a rapid, low cost method of changing the characteristics of a material surface while retaining characteristics of the bulk of the material. For example, a glass or plastic substrate material may have desirable bulk characteristics such as optical transparency, structural rigidity, or flexibility, but the surface of the substrate material may not have a desired physical or chemical property such as hydrophobicity, or an ability to interact with components of a solution applied to the substrate material. Plasma-based surface modification may alter the characteristics of a surface of the substrate material by breaking chemical bonds at the material surface. Broken chemical bonds at a material surface may react with one or more plasma species. Thus, the chemical structure of the surface may be modified and the surface may be functionalized. After functionalization, a surface of a material may have a different characteristic (such as a degree of hydrophobicity hydrophilicity) than before functionalization. Further, a functionalized surface may be able to bind to chemical compounds or biomaterials used for chemical testing, in vitro diagnostics, or point of care diagnostics.

In an exemplary embodiment, a substrate material may include a top layer of poly-methyl-methacrylate (PMMA). PMMA may be modified or functionalized by exposure of the PMMA surface to plasma containing oxygen atoms. The plasma may break surface molecular bonds, and oxygen atoms from the plasma may react with the PMMA substrate material without degrading the bulk of the PMMA substrate material. Thus, a number of carbon-oxygen bonds, including both C—O single bonds and C═O double bonds, may be greater on functionalized PMMA surface after plasma exposure than on the original PMMA surface prior to plasma exposure. New functional groups, such as the C—O single bonds and the C═O double bonds described above, may be involved in further functionalization steps to bind other compounds to a substrate material surface for analytical testing purposes or to receive chemical treatment to make materials more biocompatible. Surface modification or surface functionalization may be relevant to developing or manufacturing analytical testing devices, diagnostic probes, or medical devices.

Among the diagnostic probes and analytical devices that may be developed using plasma processing are microfluidic devices that direct the flow of small volumes of fluid through channels toward locations in the microfluidic device that are configured to perform chemical, electrical, or optical tests on the fluid. Microfluidic device manufacturing may be include one or more masking steps. Masking may be performed on a substrate surface for patterning purposes. Masking and functionalization may be performed on a substrate to induce interaction between the substrate surface (e.g., the unmasked portion) and a fluid analyte on the surface. Masking may be performed to modify a behavior characteristic of a fluid analyte (e.g., evaporation reduction by modifying surface tension of the fluid). Masking processes associated with traditional methods of surface functionalization may be performed to protect masked portions of a substrate material from surface-modifying processes while exposed portions of the substrate material surface may undergo functionalization. While masking of a surface may be advisable during manufacturing of a microfluidic device, processing conditions for removing a mask material may harm a previously-functionalized area of a surface. For example, a surface may be masked by applying a layer of photoresist to the material surface, followed by an exposure process and a developing process, wherein a pattern is formed in the photoresist layer. Plasma may be applied to the substrate to functionalize the exposed portion of the substrate, while the masked portion of the substrate is protected by the photoresist/ However, removal of the photoresist layer, typically performed by applying a solvent (such as acetone or alcohol) to the photoresist may reduce a degree of functionalization of the exposed portion of the substrate. In some embodiments, compounds used to remove photoresist may also remove the functionalization of the material surface. Further, compounds that may remove photoresist or other masking materials may be incompatible with biological materials applied to a surface, or with biological substrate materials. Organic materials or polymeric materials may also be adversely affected upon exposure to mask-removing chemistries.

Traditional plasma-based surface modification methods may involve high temperatures in plasmas and on surfaces of the substrate, may involve large currents, or may have high ion impact energies or particle velocities. In some embodiments, biomaterials such as tissues, membranes, or enzymes, may not retain desirable characteristics upon exposure to conditions associated with traditional plasmas, including high electron energy, high current, or high temperatures.

Substrate masking may also involve additional cost and manufacturing complexity to perform. For example, masking may involve additional steps in order to clean substrates, apply mask materials, pattern mask materials, and remove mask materials after a chemical or plasma surface modification is performed. Increased cost may result from at least one of additional time, additional materials, additional manufacturing equipment associated with masking, or additional cleaning steps during manufacturing. Further, additional handling and storage steps for substrates may increase facilities cost and provide opportunities for substrates to be damaged during a manufacturing process, lowering overall yield of the devices being manufactured.

In an embodiment of the present disclosure, instead of masking a substrate surface for patterning purposes, one may generate a plasma that has spatial resolution determined by the spatial characteristics of the electron beams. In a non-limiting embodiment, a plurality of directional electron beams with spatial separation may make a pattern of micro plasmas corresponding to the pattern of the directional electron beams, retaining at least some of the spatial separation of the pattern. According to an embodiment, the pattern of micro plasmas may be modified during operation of a plasma device by regulating a pattern of electron beams that form the micro plasmas. During a surface functionalization process, a pattern of electron beams/micro plasmas may be regulated to bypass areas of the substrate surface that may have already been functionalized by a plasma device or some other process. Patterning a substrate using an array of micro plasmas generated by a patterning head may lead to increased throughput processed devices because the plasma-processing volume (the working volume) has a larger cross-sectional area against a surface of a substrate than single electron-beam processing equipment.

It may be desirable to reduce cost of manufacturing objects with modified surfaces or functionalized surfaces by directly making patterns of surface functionalization on a substrate, using a plasma device with spatial separation between electron beams (or, between micro plasmas). A distribution of micro plasmas may involve gaps between individual micro plasmas, or between groups of micro plasmas. Gaps in a distribution or pattern of micro plasmas may correspond to positions, between the micro plasmas, where a surface may have undergone previous functionalization. Gaps in the distribution of micro plasmas may preserve previous surface functionalization during a subsequent surface functionalization process. A distribution of micro plasmas may undergo changes according to a position of the patterning head over a substrate being functionalized. The pattern may undergo changes according to a number of surface functionalization steps that may already have been performed in an area of a substrate surface.

Embodiments of an apparatus to perform spatially-selective nanoscale surface functionalization may include: an electron source having a grid or an array of beam sources, a gas supply system to regulate a chemical composition of a working volume where a plasma can form, and a movement system to regulate a position and alignment of a substrate with regard to the patterning head of a plasma device. Some embodiments of the apparatus may also include a gas delivery system wherein a gas or liquid, or combinations thereof, may be added to a working volume in order to modify the gas composition (and, therefore, a type of surface functionalization.

Spatial resolution of micro plasmas may decrease the number of manufacturing steps involved in generating surface-modified or surface-functionalized devices, increasing device manufacturing throughput. Spatial resolution of micro plasmas may enable plasma modification and functionalization at pressures above the range of previously available plasma modification devices (e.g., at or around atmospheric, or 1 bar of pressure. For example, during a manufacturing process, a plasma-based surface modification device may pattern a substrate by positioning a patterning head of the plasma device in proximity to a substrate and performing plasma-based service modification at atmospheric pressure, or at pressures ranging from about 0.5 to 2 atmosphere (atm), without damage to the substrate during a modification process. The ability to operate a patterning head of a plasma device at approximately atmospheric pressure may greatly reduce manufacturing time because a substrate may be modified without placing the substrate in a pressure chamber having reduced or elevated pressures, reducing the need for chamber palm down or chamber purging times.

In some embodiments, a patterning device may be operated with an adjustable gas mixture and or plasma composition, at approximately atmospheric pressure, by directing a flow of gas or a flow of atomized or evaporated liquid, into a working volume between a portion of the patterning device where the plasma is generated and an area of a substrate where service modification is being performed. By adjusting the chemical composition of the gaseous mixture before plasma generation and during plasma generation, the chemistry of a substrate surface may be regulated to generate predetermined distributions of surface functionalization according to the chemical composition of the plasma.

A patterning head having spatial control of the plasma above a surface during a modification process may involve generating a plurality of micro-plasmas arranged in an array between the patterning head and the surface of the substrate. The micro-plasmas may remain discrete, or may merge to form larger plasmas. The working volume between a patterning head and a substrate being modified during a manufacturing process may contain a plurality of volumes, each of which may contain an individually adjustable micro-plasma. Thus, each volume may have a micro plasma that is turned off or turned on independent of other volumes with other micro-plasmas (e.g., the micro plasmas, or the array loci at which micro plasmas may be generated, may be individually addressable). Thus, spatial control of the plasma in the working volume may afford greater manufacturing flexibility during modification of the process to functionalized only a desired and controllable portion of a substrate while leaving other options of the substrate unmodified by the present plasma modification process.

A patterning head may include an electron source that generates directional beams of electrons. An electron source may include one or more emission structures that generate electrons that can form directed beams. Emission structures may include thermionic emission structures, field-emission (FE) structures, or pyroelectric (PE) structures. Thermionic emission structures may generate beams of electrons after the structures are heated in the present of a strong external electrical field that can accelerated the emitted electrons from the thermionic emission structures toward a substrate surface outside a patterning head. Field emission structures may involve electron emission in the presence of a strong electrical field (stronger than for thermionic emission structures), but at lower temperatures for the emission structures (as compared to thermionic emission structures). Pyroelectric (PE) structures may generate electron beams following rapid thermal cycling of PE structures with large thermal gradients, in the presence of an accelerating voltage that is significantly smaller than the accelerating voltage for either thermionic emission or FE emission.

Electron emission structures may occur singly, or in clusters, at a location in an electron source. In an embodiment, electron emission structures may occur in arrays, where each locus of the array, whether populated by a single electron emission structure or by a cluster of electron emission structures, may be individually addressable (e.g., each locus may be regulated independent of each other locus of the array). Thermionic electron emission structures may consume more energy to generate an electron beam than do FE or PE electron emission structures because of the elevated operational temperatures. FE electron emission may use an intermediate amount of energy, resulting from the strong electrical fields applied within the patterning head, to trigger electron beam formation. PE electron emission may use less energy than either thermionic electron emission or FE electron emission because electrons collect on emission structures and may be accelerated with lower voltages than for thermionic emission or FE emission. FE and PE nanostructures may be more compatible with organic materials, polymeric materials, or biomaterials than traditional methods of producing plasma to modify a surface.

Electron sources with field emission nanostructures tend to operate at much lower temperatures than either thermionic or DBD plasma sources, to the extent that the process is dubbed "cold emission". Electron emission structures, as disclosed herein, may generate directional electron beams without use of magnetic lenses to focus and direct the beam of electrons onto a substrate. A patterning head without magnetic lenses may be considerably smaller a plasma device that uses magnetic lenses to focus a beam. By omitting magnetic lenses from a structure containing an electron source, the manufacturing cost of the plasma device may be considerably reduced. Individually addressable electron emission structures may result in formation of micro plasmas in a working volume outside of a patterning head of a plasma device when a directed electron beams strikes a primed atmosphere. Directed beams of electrons may be accelerated by an electron accelerating structure into the primed atmosphere with an energy associated with the potential difference between the electron emission structure and the electron accelerating structure. Directed beams of electrons may be focused by optional beam control apertures that expand or compress a distribution of the directed beams around a center point of a path between the electron source and the substrate FIG. 1 depicts a cross-sectional diagram of an embodiment of a spatially selective surface functionalization device, or a plasma device, 100. While the embodiment described herein may be representative of other embodiments, not all features of the plasma device 100 may be present in each other embodiment of the present disclosure that is described herein. Conversely, other embodiments of a plasma device may have additional elements that are not described in the embodiment of FIG. 1, but may still contain aspects of the present disclosure sufficient to fall within the scope of said disclosure.

Plasma device 100 may contain a movement system (or stage) 102, on which a substrate 104 may be situated for surface functionalization, located below a patterning head 106. During operation of plasma device 100, patterning head 106 may generate plasma 108 in a working volume 110 between a window 112 of the patterning head 106 (through which a directed beam of electrons 114 may pass to trigger plasma formation) and the substrate 104. During operation of plasma device 100, the patterning head 106 may be situated a working distance 115 above a top surface of substrate 104. Working distance may range from about 10-micron to a 1 millimeter, according to embodiments of the present disclosure. In some embodiments, a working distance may increase or decrease during surface functionalization of the substrate according to a plasma density within the working volume, according to the size of the pattern being formed on the substrate, or according to a composition of the plasma during surface functionalization.

The patterning head 106 of plasma device 100 may include an aligner 116 configured to adjust pitch (parallelism between patterning head and substrate) and orientation (provides rotational control of the substrate beneath the patterning head) of the patterning head 106 with regard to the movement system 102 and a substrate 104 located thereon.

Movement system 102 may be configured to adjust a lateral position of the patterning head 106 and any substrate thereon with regard to the patterning head 106. Movement system 104 may be configured to move continuously, or to move incrementally, below the patterning head 106. Incremental movement of the substrate below the patterning head may be beneficial for functionalizing discrete blocks of substrate material on a top surface of the substrate, where the blocks or regions of the top surface do not contain structures that extend continuously between adjoining blocks. Continuous movement of the movement system, and the substrate material, below the patterning head may be beneficial for functionalizing, on a top surface of the substrate, patterns that have continuous extensions across borders of adjoining blocks or regions of a substrate top surface. According to some embodiments, functionalizing a substrate material top surface may involve a process of gradual modification of a distribution of micro plasmas in the working volume between the patterning head and the substrate. According to some embodiments, functionalizing a substrate material top surface may involve forming a first distribution of micro plasmas within a working volume, extinguishing the micro plasmas, adjusting a position of the patterning head over the substrate, and re-ignition of a distribution of micro plasmas at a second position of the patterning head at a second position above the substrate.

Micro plasmas may be formed in working volume 110 between the patterning head 106 and the substrate 104 by a directed beam of electrons 114 emitted by an electron source 118 located in a cavity 120 of an electron source housing 122. A membrane 124 may be located between electron source 118 and the working volume 110. An electron accelerating structure (or, accelerating structure) 126 may be located in a plane below a bottom surface of the electron source 118. Having the electron source 118 positioned "above" the electron accelerating structure 126 may allow the electrons generated by the electron source 118 to be accelerated by a positive voltage on the electron accelerating structure 126 such that the electrons achieve a desired electron energy (measured in electron volts, or eV) as the electrons pass through the membrane 124 and the window 112 before striking atoms and molecules in the working volume to trigger plasma formation.

According to embodiments, electron source 118 may have a plurality of individually addressable electron emission structures located therein, each capable of generating a beam of electrons that may be accelerated toward the membrane 124 and window 112 into working volume 110.

Electron accelerating structure 126, electron source 118, aligner 116, and movement system 102 may receive electrical power from a power supply 128 over electrical connections 130. Electron accelerating structure 126 may receive an electrical voltage configured to attract electrons from electron source 118 out of electron source 118 and toward working volume 110 and substrate 104. According to some embodiments, an electron accelerating structure may operate with an electrical voltage less than an electrical voltage ranging from about 1 kV to about 50 kV, such that electrons exiting an electron source may have an electron energy ranging from about 1 keV to about 50 keV. An electron accelerating structure may have a coating of thin films to prevent discharging between the electron accelerating structure and components of the plasma device, including the electron source and electron emission structures located therein. An electron accelerating structure may be made of one or more metals, or layers of metals, or alloys of multiple metals, such as copper, aluminum, tungsten, titanium, or platinum.

A plasma device may have a control element 132 (or a pattern management system) configured to handle information regarding the relative positions of movement system 102, substrate 104, and aligner 116, as well as regulating information about the pattern being functionalized on a top surface of the substrate and the formation of the plasma, or micro plasmas, in the working volume 110 during surface modification and/or functionalization. Control element 132 may include a communication bus 134, a pattern repository 136, a pattern buffer 138, a emission structure activation element 140, and an instruction generator 142. Control element 132, or the subcomponents of control element 123, including emission structure activation element 140, may be programmable to convert a pattern, or a portion of a pattern, into a dynamically updated pattern of electron beams and micro plasmas during patterning head operation. Communication bus 134 may interconnect pattern repository 136, pattern buffer 138, emission structure activation element 140, and instruction generator 142 to each other and to aligner 116, electron source 118, and to movement system 102 in order to facilitate regulation of substrate position, alignment, or orientation, and to regulate formation, adjustment, or extinguishing of plasmas or micro plasmas below patterning head 106 in working volume 110.

Pattern repository 136 may be configured to receive, over a data connection or input/output port, information regarding a pattern to be formed during a surface functionalization process on a top surface of substrate 104. The pattern may include information regarding the boundaries and shapes of areas or regions on a substrate top surface, the type of functionalization that is intended for each area or region on the substrate top surface, and the processing conditions (including plasma composition, electron energy, plasma density, working distance, exposure time, and micro plasma pattern regulation parameters) that can produce a region of surface functionalization on the substrate top surface.

Pattern buffer 138 may include a storage medium such as DRAM (dynamic random access memory), a hard disk drive, a solid state drive, or some other form of volatile or non-volatile storage medium where information regarding a portion of one or more patterns stored in the pattern repository 136 may be transferred and manipulated in order to perform a surface functionalization process. Information regarding the portion of one or more patterns in a pattern repository may be transferred from a pattern repository to a pattern buffer for manipulation and communication to an instruction generator 142. Further, information regarding the completion status of surface functionalization of a substrate, or a portion thereof, may be stored in a pattern buffer and communicated back to the pattern repository in order to facilitate transfer from the pattern repository to the pattern buffer of another portion of one or more patterns.

Instruction generator 142 may be connected to pattern buffer 138 over communication bus 134 in order to receive a portion of the information regarding a portion of one or more patterns stored in the pattern buffer. Instruction generator 142 may be programmable, configured to analyze the information and to generate, based on the information regarding the pattern, and on previous, present, or upcoming processing conditions for surface functionalization, on the material of the substrate 104, on the progress in functionalizing a surface of the substrate with the pattern, and on a position of the substrate with regard to the patterning head 106, instructions for performing current or upcoming surface functionalization steps. According to an embodiment, the instructions may include instructions on a rate of motion of the substrate below the patterning head, instructions on modifying a working distance between the patterning head and the substrate, instructions about modifying a composition of the gas mixture in the working volume, instructions about retaining a distribution of micro plasmas within the working volume, or about modifying a distribution of micro plasmas, instructions about modifying an accelerating structure voltage to modify electron energy within the working distance, or instructions about a type of motion of the substrate with respect to the patterning head (i.e., continuous or step-wise motion of the substrate, and instructions regarding modifying a degree of focus (or, of a degree to which a distribution pattern of micro plasmas is compressed before the pattern impinges on the top surface of the substrate.

A distribution of micro plasmas generated by the patterning device may be modified by instructions from the instruction generator 142 to a nanostructure activation element 140 for regulation of the pattern of electron emission structures that emit electron beams in an array of electron emission structures of an electron source. An instruction to a emission structure activation element may include further instructions regarding the activation or deactivation of individual electron emission structures (or, loci having clusters of emission structure structures): when an instruction is performed by the emission structure activation element, some emission structures may become activated, some may become deactivated, some may remain activated, and some may remain deactivated, according to the pattern of functionalization being performed at the time of the instruction performance, and according to a position of the substrate below the patterning head.

Patterning head 106 may further include one or more nozzles (or micro nozzles, or orifices) 144, connected to one or more reservoirs 146 with a flow regulator 148, configured to supply a fluid mixture to the working volume 110 between patterning head 106 and substrate 104. According to an embodiment, a supply of fluid (a gas or a liquid) to the working volume during surface modification may adjust the chemical composition of the substrate top surface during the surface modification process. According to an embodiment, a fluid mixture may include one or more gaseous species, or may include a volatilized (or aerosolized) liquid that, upon evaporation, provides a gaseous component for the gas mixture. Chemical species that may be used for surface functionalization include compounds for increasing a concentration of surface oxygen on a substrate surface, compounds for increasing a concentration of a halogen on a substrate surface, and compounds for increasing a concentration of nitrogen on a substrate surface. Chemical species that functionalize a surface may be radicals or nonradicals. Chemical species that may promote functionalization of a surface with halogen atoms, including chlorine or bromine, may include atomic chlorine or atomic bromine, or non-radical species such as: hypochlorous acid (HOCl), nitryl chloride ($NO_2Cl$), chloramines, chlorine gas ($Cl_2$), bromine chloride (BrCl), chlorine dioxide ($ClO_2$), hypobromous acid (HOBr), or bromine gas ($Br_2$). Chemical species related to addition of oxygen to a substrate surface may include radicals or non-radical species, such as: superoxide ($O_2^{\cdot-}$), hydroxyl radicals (HO$^{\cdot}$), hydroperoxyl radical ($HO_2^{\cdot}$), carbonate ($CO_3^{\cdot-}$), peroxyl radicals ($RO_2^{\cdot}$), where R is a carbon or other atom, and alkolxyl radicals (RO$^{\cdot}$), where R is a carbon or other atom, as well as nonradical species such as hydrogen peroxide, hypobromous acid (HOBr), hypochlorous acid (HOCl), ozone ($O_3$), organic peroxides (ROOH), where R=C, poroxynitrite (ONOO−), or peroxynitrous acid (ONOOH). Chemical species related to addition of nitrogen to a substrate surface may include species such as nitric oxide NO•, nitrogen dioxide $NO_2$•, nitrate radical ($NO_3$•), nitrous acid ($HNO_2$), dinitrogen tetroxide ($N_2O_4$), dinitrogen trioxide ($N_2O_3$), peroxynitrite (ONOO−), peroxynitrous acid (ONOOH), or nitryl chloride ($NO_2Cl$).

Nozzles 144 may have a pressure that is greater than the pressure of ambient atmosphere in the working volume. In some embodiments, nozzles may have a pressure that is lower than the pressure of ambient atmosphere. Nozzle pressures below ambient pressure may allow evacuation or flushing of the working volume, removing spent or reacted gases and byproducts from the working while some nozzles with pressures above ambient pressure supply new fluids (e.g., gases or aerosolized liquids) for surface functionalization. By adjusting the pressures of the nozzles, plasma in the working volume may be reshaped, or resized, in order to adjust the pattern of surface functionalization during substrate processing. Nozzles may be arranged along opposite sides of the patterning head, in some embodiments. In an embodiment, nozzles may be arranged around a perimeter of the patterning head. Nozzle pressures may be regulated independently, or in groups, according to some embodiments of the present disclosure. Regulating nozzles in groups may reduce a number of fluid handling components (e.g., flow regulators, reservoirs, supply lines, etc . . . ).

Figure 2:
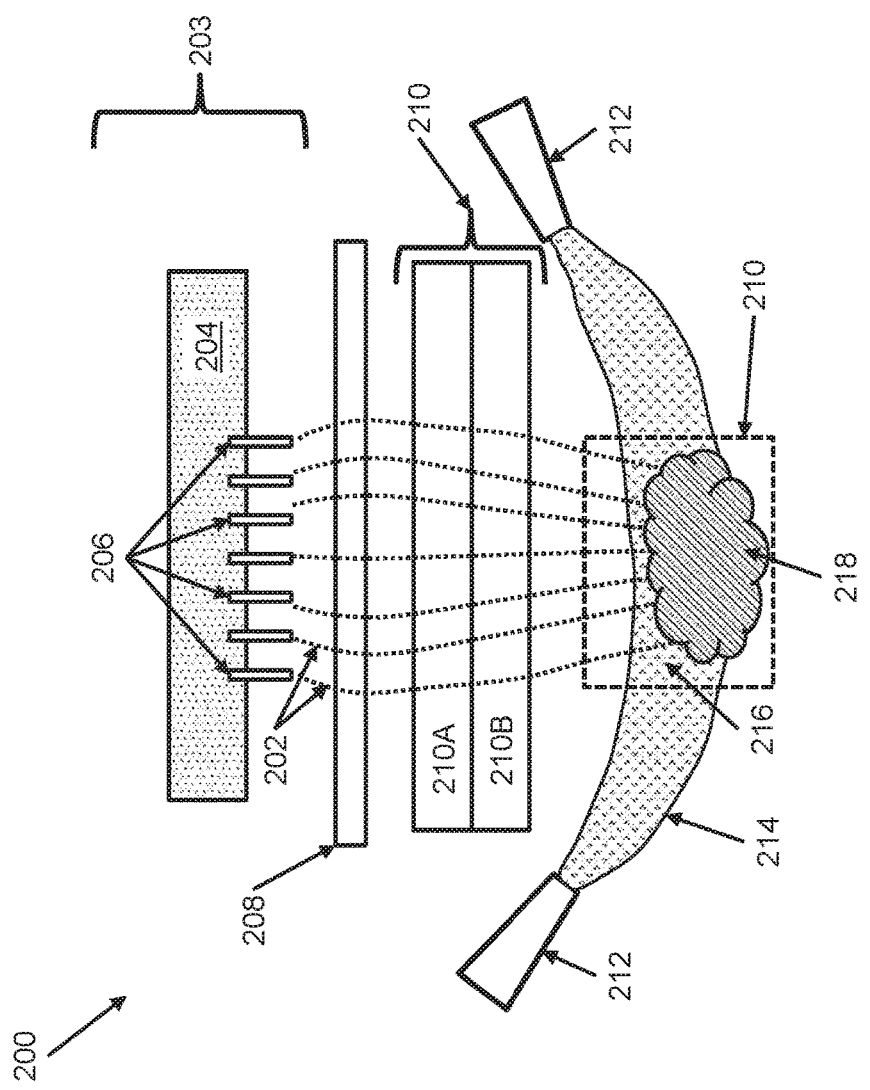
FIG. 2 depicts a cross-sectional view of an embodiment of apparatus for generating micro plasmas using electron emission structures.

FIG. 2 depicts a cross-sectional view of an embodiment of a patterning head 200 having field emission structures. The cross-sectional view includes a depiction of a path traveled by directed beams of electrons 202 outward from a chip 203 of the electron source 204. Chip 203 includes at least one field emission structures 206, the at least one field emission structure being oriented downward toward an electron accelerating structure 208, a membrane 210, and a working volume 219. The directed beams of electrons 202 may intersect a primed gas mixture 216 in working volume 219, composed at least partially by a gas 214 emitted by one or more nozzles 212 oriented toward working volume 219. Plasma 218 may be formed by the intersection of directed beams of electrons 202 with primed mixture 216 in working volume 219.

Electron source 204 may be a sealed structure with the field emission structures at an electrical potential less than the electrical potential of an electron accelerating structure 208. Electron source 204 may, upon application of a positive electrical potential to the electron acceleration structure 208, and upon application of a negative electrical potential to field emission structures, cause directed electrons to travel toward a substrate for plasma formation. Upon passage of directed electrons through the membrane 210 and into the working volume, one or more micro plasmas may be formed in a working volume. The working volume may be a controlled region that can undergo spatial adjustment (as by, for example, modifying a working distance between a substrate and the patterning head), by regulating the gas temperature, by regulating the gas composition, or by adjusting a flow rate of the primed mixture in the working volume.

In some embodiments, an electron mask (not shown) may be positioned in the path of the directed electron beams in order to absorb some of the electrons while passing other of the electrons, forming a patterned plasma in the working volume. One advantage to using individually controllable field emission structures of an electron source is the ability to dynamically reconfigure a distribution or pattern of micro plasmas within the working volume without removing or replacing a physical electron mask of the patterning head.

According to some embodiments, the chip 203 may be a substrate material with an interleaved conductive network that makes contact with the FE nanostructures of the electron source. The chip substrate material may be made of one or more of silicon, silicon dioxide, quartz, or some other combination of semiconducting and dielectric materials that provide insulation between elements of the interleaved conductive network that provides a conductive path between the field emission structure and the power source of the patterning device.

Field emission structures 206 may include silicon nanowires, silicon carbide nanowires, carbon fiber nanowires, carbon nanotubes, or some other conductive material. Field emission structures may be deposited onto conductive pad areas of the chip. In some embodiments, field emission structures may be grown in situ on conductive pad areas of the chip. According to an embodiment, field emission structures may be formed by seeded growth, self-organized assembly, or adhesion of emission structures to a conductive pad of the electron source. Field emission structures may have distal ends extending toward the electron accelerating structure of an electron source. Upon exposure of the field emission structures to an attracting (positive) voltage at the electron accelerating source, individual field emission structures, or loci of field emission structures in an array of conductive pad areas of the chip, may, when at a negative potential individually (or, as a group when a plurality of field emission structures are located at a single locus of the array) emit electrons. In an embodiment, a voltage applied to at least one locus in an array of field emission structures, or to at least one field emission structure, may be between about −1 kV and about −10 kV in order to promote formation of a beam of directed electrons during surface functionalization and/or surface modification processes. Electron emission from the field emission structures may be modified dynamically by instructions supplied by the instruction generator to the field emission structure activation element of the control element of a patterning device.

Electron accelerating structure 208 may be a mesh or a ring structure held at a positive voltage with respect to the field emission structures 206 of the electron source 202. An electron accelerating structure may be located within the electron source 202 in proximity to the field emission structures such that the electrical field strength at the field emission structures is sufficient to allow electrons to escape from the field emission structures without elevated temperature (as would be the case with thermionic emission electron sources) or significantly large voltage differentials (as would be the case with a DBD electron sources). According to an embodiment, an electron accelerating structure may be made of a metal, such as tungsten, copper, aluminum, titanium, platinum, or another metal suitable for shaping into a mesh or ring structure within the electron source. In some embodiments, the metal may be corrosion resistant to withstand impacts of directed electron beams and to avoid oxidation/reduction reactions of the metal with any gas present within the patterning head. Electron accelerating structure 208 may be used to extract electrons from the electron source, accelerate electrons toward the substrate, focus electrons into a smaller area than the area of the array of FE nanostructures, or scan the directed beams of electrons across a region of a membrane or across the working volume during operation of the plasma device.

Membrane 210 may include a first membrane face 210A and a second membrane face 210B, with the first membrane face closer to the FE nanostructures and the second membrane face closer to the substrate. In an embodiment, first membrane face may be a conducting layer and second membrane face may be a non-conducting layer. In an embodiment, first membrane face 210A may be made of a conducting material, or alloys of conducting metals, such as copper, aluminum, tungsten, titanium, or platinum. In an embodiment, second membrane face 210B may be made of a non-conducting material such as silicon dioxide or silicon nitride or another insulting material. The combination of the emission structures 206 and electrodes 210A and 210B may be considered a triode arrangement. According to an embodiment, one of the membrane faces may be formed by deposition, either by sputtering, chemical vapor deposition, epitaxial growth, or electrochemical deposition, of one of the materials a membrane face on a thicker layer of material of the other membrane face. For example, a metallic layer may be formed by sputtering or electroplating of a metal such as tungsten, on a thicker layer of silicon nitride, to form a tungsten/silicon nitride membrane. Other combinations of conducting and non-conducting membrane combinations may be readily apparent to practitioners of the art using common deposition and film-growth techniques.

Electrons can penetrate through a thin membrane if their kinetic energy is much larger than the energy lost in the membrane material by collisional scattering. Typically, these membrane are made of conductive manufacturable material including, but not limited to, metals such as Ti, Cu, W, or conductive organic materials such as carbon, graphene, fullerene-like materials, or carbon nanotubes. A combination of electron energy ranges and membrane ranges are generally 5,000V to 20,000V and 1 nm to 100 nm, respectively. In some manifestations, a thin dielectric material is added to assist in the fabrication of the conductive membrane and act as backing to the membrane, the thickness of the dielectric satisfies the condition for small relative loss of the electron beam energy in the dielectric, typically this dielectric is SiN or similar material and is less than 300 nm thick.

As described previously, directed electron beams 202 emitted from field emission structures 206 may be directed downward into a working volume 210 to generate a plasma comprising ionized gaseous species. Composition of the plasma may be modified by modifying, during surface modification, a chemical composition of the primed gas mixture in the working volume 219. One benefit of a lower voltage electron source such as a sealed electron source having a chip with field emission structures may be that the primed gas mixture may be a static, or stationary, gas mixture. The plasma, or micro plasmas, formed in the working volume may be formed with little or no arcing or pressure fluctuations because of the lower electron energies for field emission electron sources, as compared to other electron sources such as thermionic emission electron sources. Further, because plasmas may be formed with static gas mixtures present in the working volume, with gas flow rates ranging from about 1 ml/min to about 100 ml/min.

Figure 3:
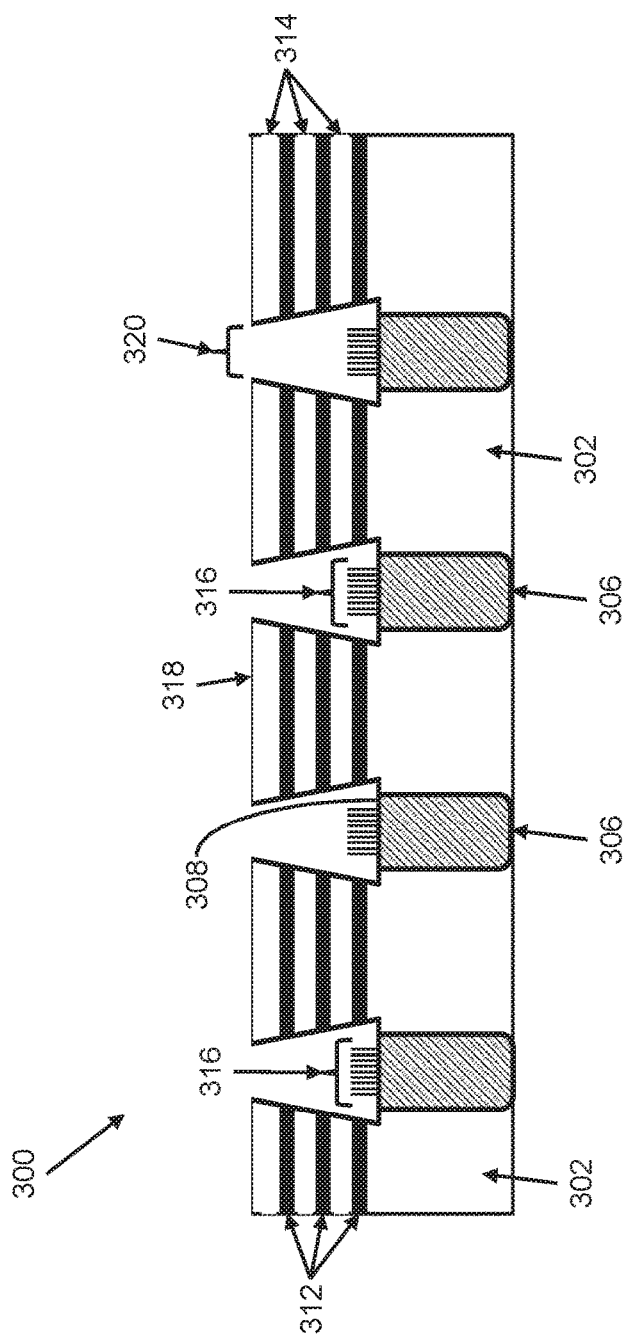
FIG. 3 depicts a cross-sectional view of an embodiment of a chip having electron emission structures.
Figure 8:
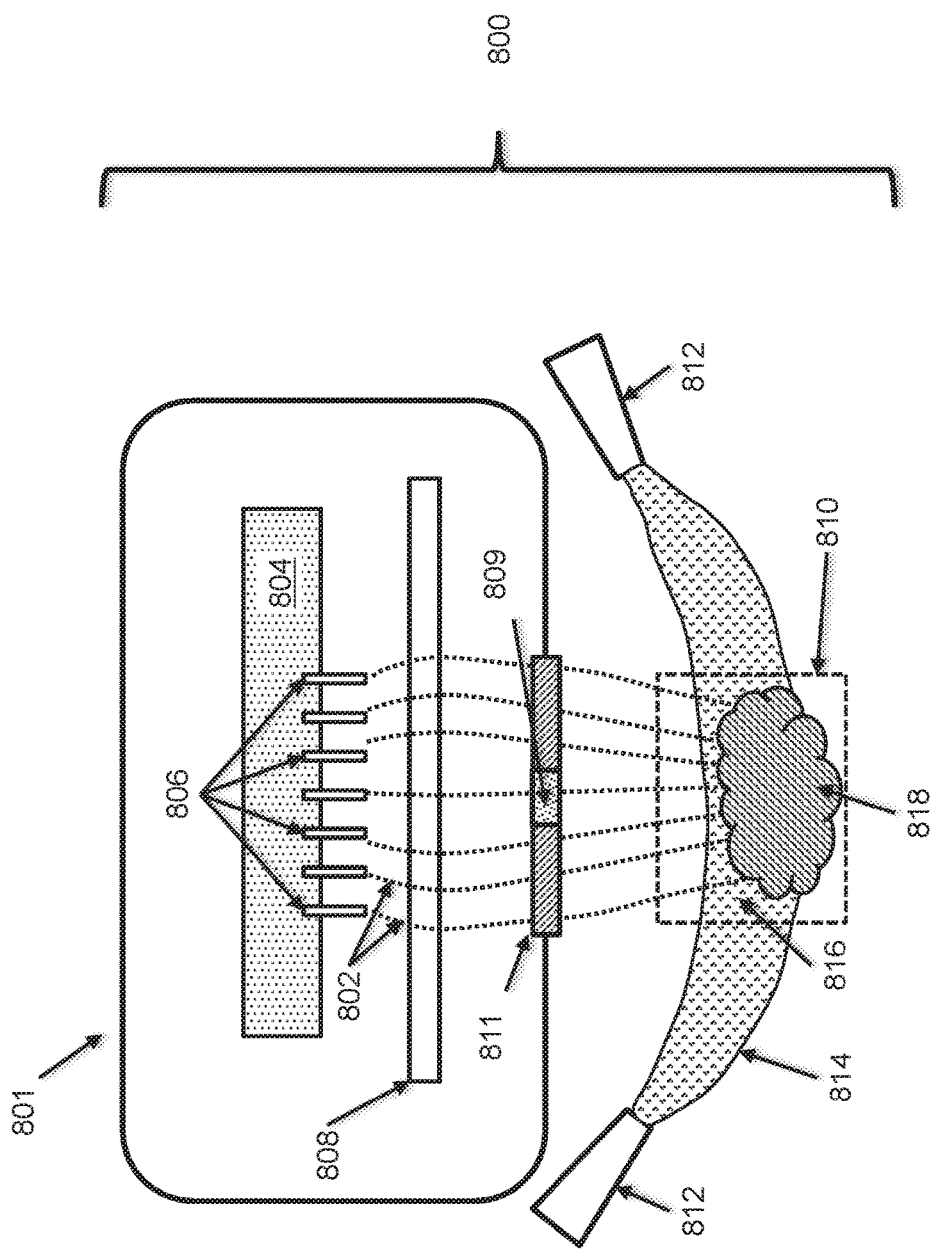
FIG. 8 depicts a plasma device having an array of emission structures of an electron source substrate.

FIG. 8 depicts a plasma device 800 having an electron emission structure array 806 in an electron source substrate 804. In some embodiments, the electron source substrate may be a chip comprising semiconductor materials with nanostructures located thereon as depicted in FIG. 3, below. Electron emission structure array 806 may include diode structures configured to generate electron beams 802. Electron source substrate 804 and electron emission structure array 806, as well as electron accelerating structure 808, may be located within a sealed enclosure 801, configured to operate at a first pressure in the sealed enclosure that is lower than an external pressure outside the sealed enclosure. Electron accelerating structure 808 may be a conductive material such as a mesh or thick conductive membrane. Some embodiments of electron accelerating structures may include materials that are simple to manufacture into mesh or ring-like structures, including titanium, copper, tungsten, graphene, etc . . . Electron accelerating structure 808 may extract electrons from nanostructures in the electron emission structure array 806 by holding, during operation of the plasma device, a positive voltage, while the nanostructure of the electron emission structure array 806 may hold a negative voltage. Electron accelerating structure may also serve to accelerate extracted or emitted electrons from the nanostructures along a path toward sealing membrane 811 and working volume 810 (outside the sealed enclosure 801).

Electron accelerating structure 808 may be kept at a potential that is less negative than the substrate 804 and the electron emission structure 802 combined. As a non-limiting example, the substrate 804 can be held at potential between about −1 kV and about −10 kiloVolt (kV) with electron accelerating structure 808 grounded (0 V). The final electron energy of electrons in electron beams 802, as they exit sealed enclosure 801, may be a function of the total potential difference between the electron accelerating structure 808 and electron source substrate 804.

The distance between the electron source substrate 804 and the electron accelerating structure 808 may be significantly smaller than a lateral measurement (length, width) of the electron source substrate 804. A ratio of about 5:1 (lateral measurement to separating distance) may be desirable in order to maintain a uniform electric field and to promote formation of parallel beams of electrons upon electron emission from nanostructures of electron source substrate 804. The ratio may be as much as 10:1, while still maintaining uniform electric fields in the plasma device. Ratios smaller than about 5:1 may lead to significant electric field distortions. As with patterning head 200, sealed enclosure 801 may have an interior pressure smaller than the exterior pressure. A sealing membrane 811 or, in some embodiments, a hard aperture (not shown) capable of active differential pumping, may be used. A hard aperture may further serve to confine the electron beams 802 in a lateral dimension. Working volume 810, nozzles 812, gases 814, and primed mixture 816, the plasma formation 818 are similar to the description of corresponding elements of FIG. 2, wherein the numerals are incremented by 600.

Figure 9:
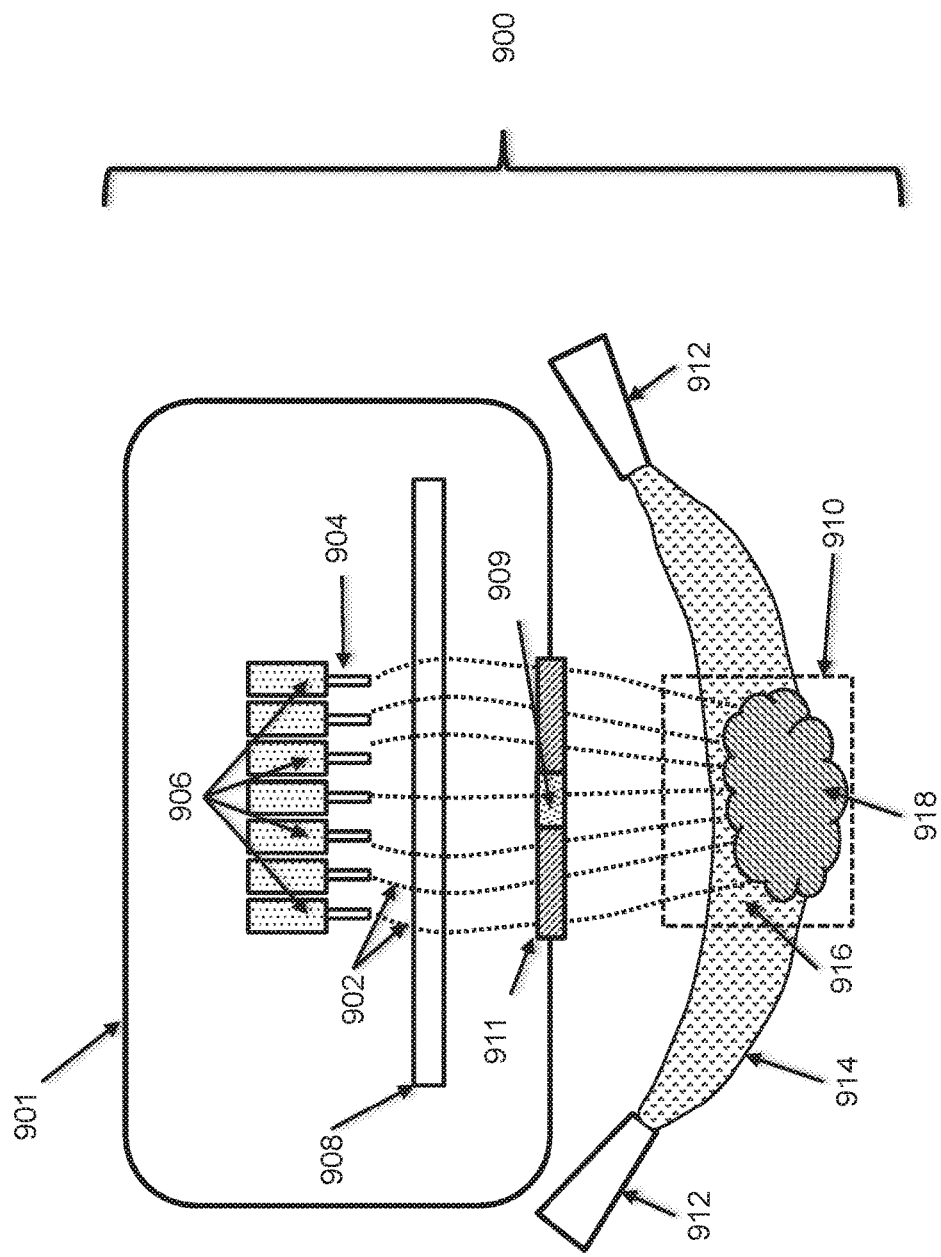
FIG. 9 depicts an embodiment of a plasma device having a plurality of pyroelectric emission structures.

FIG. 9 depicts an embodiment of a plasma device 900 having a plurality of pyroelectric (PE) electron emission structures (pyroelectric crystals) 904 located within sealed enclosure 901. Pyroelectric electron emission structures 904 may be situated at a distal end of individually addressable thermal elements 906, the distal end being closer to the electron accelerating structure 908 than to a wall of the sealed enclosure 901. Pyroelectric electron emission structures may be made of materials including, but not limited to, lithium niobate ($LiNbO_3$), lithium tantalate ($LiTaO_3$), or barium titanate ($BaTiO_3$).

Individually addressable thermal elements 906 may be configured to undergo large amplitude, high gradient thermal changes to generate, within the pyroelectric nanostructures, a residual electrical charge on individual pyroelectric nanostructures. Individually addressable thermal elements 906 may include one or more micro heating elements and one or more micro cooling elements, configured to rapidly modulate a temperature of the individually addressable thermal elements, and the pyroelectric nanostructures located thereon, to induce electron accumulation on the PE electron emission structures. A number of micro heating element sand micro cooling elements in an individually addressable thermal element may be determined according to the chemical structure of the PE electron emission structures located thereon, and the individual electron accumulation characteristics of the PE electron emission structure material.

Electrical charges accumulated on PE electron emission structures may be induced to leave the PE electron emission structures and travel through the sealed enclosure in directed electron beams. An electron accelerating structure 904 may trigger departure of electrons from PE electron emission structures, and may accelerate the electrons toward a substrate in order to cause plasma formation above a substrate surface. PE electron emission structures may be held at a negative voltage of between about −2 kV and about −10 kV, and an electron accelerating structure may be held at a positive voltage of about +10 kV, in order to promote electron beam formation and to regulate electron energy in the plasma formed in working volume 910. Pyroelectric emission may occur at pressures within the sealed enclosure 901 of about 1 Torr, although other pressures may be employed according to voltage configurations of the plasma device and the identity of the gas within the sealed enclosure. Pyroelectric emission may occur with voltages that are significantly lower than thermionic emission or DBD electron sources, reducing a cost of manufacturing of materials using a plasma device as disclosed herein.

Individually addressable thermal elements, and pyroelectric electron emission structures 904 located thereon, may be arranged in an array having a plurality of loci, each locus being individually addressable to trigger electron emission from one locus independent of electron emission status at a second locus within the array. Elements of FIG. 9 not mentioned above resemble the corresponding elements of FIG. 2, having identifying numbers incremented by 700.

FIG. 3 depicts a cross-sectional view of an embodiment of a chip 300 of an electron source. Chip 300 comprises a substrate 302 having a plurality of electrical connections (not shown) extending through the substrate 302 and connecting to a nanostructure activation element in a controller element (or, a pattern management system) of a plasma device as described previously. Electrical connections may include a plurality of contacts 306 or pads having a contact top surface 308 that is exposed. Spatial selectivity of the patterning device may relate to the pitch between contacts 306 of an electron source, and to the ability of a nanostructure activation element to, upon receiving an instruction from an instruction generator of a controller element (see FIG. 2, above), modify the activation status of individual FE nanostructures (or, of FE nanostructures at a single locus in an array of contacts having FE nanostructures on the top surfaces of the contacts.

According to some embodiments, a remainder of a contact (the portion other than the contact top surface) may be surrounded by substrate material or other materials of the chip. The substrate 302 may have a substrate top surface 308 that is covered by layers of material 312 and 314 that insulate the contacts 306 and electrical connections from the electrical field of an electron accelerating structure of the electron source. In an embodiment, a contact top surface may be approximately coplanar with a substrate top surface. According to an embodiment, a contact top surface may be recessed below a substrate top surface. In an embodiment, a contact top surface may extend above a substrate top surface.

Contact top surface 308 may be covered by one or more electron emission structures 316 from which a directed beam of electrons may be drawn by an electron accelerating structure of an electron source. Electron emission structures 316 may include nano rods, nanowires, carbon nanotubes, fullerene-like structures, tunneling cold field emitter cathodes, or diode structures. Electron emission structures may be made from materials that include silicon, silicon carbide, carbon nanotubes, fullerenes, or pyroelectric materials. The electron emission structure array in chip 300 may have a low impedance in order to facilitate electron emission from the chip toward the electron accelerating structure. Impedance may be low enough that thermal loading is reduced and thermal damage to a chip or nanostructures thereon is reduced. In some embodiments, the activation voltage for field emission from electron emission structures may be less than or equal to about 1 keV. Electron emission structures as described herein may reduce power consumption of a patterning head, as described above, to wattages below about 5 Watts. In some embodiments, power consumption may be reduced to below 1 Watt of power.

Electron emission structures 316 may be located below a chip top surface 318 within chip openings 320. A working distance between chip top surface 318 and a substrate surface during surface functionalization may range from 0 mm to about 1 mm, or more, while plasma modifies or functionalizes a substrate surface.

FIG. 4 depicts a cross-sectional analysis of an embodiment of plasma device 400. Plasma device 400 is shown, separated from a substrate 402 by a working distance 404, during a surface functionalization process. A plasma 406 may be formed in a working volume 408 upon ignition of the plasma by a directed beam of electrons 410 in a gas delivered to the working volume 408 by a gas supply nozzle 412. Directed beam of electrons 410 may be emitted by an electron emission structure 416, upon formation of a large positive electrical voltage by an electron accelerating structure 414, in proximity to electron emission structure 416. Directed beam of electrons 410 may be drawn from the electron emission structure 416 by the electron accelerating structure 414, through a control ring (or control mesh) 418 and through a membrane and/or window 418.

A dimension of the plasma 406 may be regulated by beam defining aperture 420, configured to electromagnetically compress or expand the directed beam of electrons 410 during passage through membrane and/or window 418 and formation of plasma 406. In some embodiments, a dimension of the plasma may be increased by the beam defining aperture to expose a larger dimension of substrate to plasma during surface functionalization. In an embodiment, a dimension of a plasma may be reduced in order to generate smaller features and to restrict plasma-induced damage, or the likelihood thereof, upon sequential surface functionalization steps on a substrate top surface.

Plasma device 400 may have an electron scanning element 422 configured to steer directed beam of electrons 410 across a top surface of substrate 402 during surface functionalization. By regulating the strength of an electromagnetic field of beam defining aperture 420, a position of substrate 402, and a magnitude of electromagnetic fields of electron scanning element, an electron beam (or beams, according to a number of electron emission structures in plasma device 400), may scribe plasma across a top surface of substrate 402 with spatial separation from already-functionalized regions of the top surface of substrate 402. According to a pitch between electron emission structures of the plasma device, and according to the magnitude of the beam definition field, inter alia, an array of directed electron beams may be "compressed" into a distribution of directed electron beams having a separation between adjacent directed electron beams measured in units of micrometers or nanometers. A pitch between individual loci for electron emission structures may range from about 10 nm to about 1 mm, and a pitch between loci in an array of nanostructure clusters on a surface of an electron source substrate may range from about 100 nm to about 1000 micrometers. A pitch of directed electron beams may range from about 250 nanometers (nm) to about 1 millimeter (mm) according to an embodiment. According to an embodiment, a second beam defining aperture (not shown) may be used to contain a plasma (or, a plurality of micro plasmas) formed in a working volume 408 between plasma device 400 and a substrate 402.

An electron emission structure 416 (or, an array of electron emission structures) may be formed on a low impedance substrate 424 of plasma device 400. In some embodiments, low impedance substrate may be a chip such as chip 203 of FIG. 3, described above. Low impedance substrate 424 may be located within an electron source housing 426. An electrical connection 430 may be connected to low impedance substrate 424, and consequently to the electron emission structure 416 (or, the array of electron emission structures) thereon as a source of electrons for the electron beam.

Electron source housing 426 may be under vacuum in an embodiment, Electron source housing 426 may be at a pressure less than ambient atmospheric pressure. Electron source housing 426 may have a gaseous composition that is different from the gaseous composition of ambient atmosphere outside of plasma device 400. Electron source housing 426 may have a gaseous composition that is different from the gaseous composition of the working volume between the patterning head and a substrate. A pressure of within plasma device 400 may be reduced below the ambient outer pressure by withdrawal of gas from an interior of plasma device 400 through a vacuum port 428.

Figure 5A:
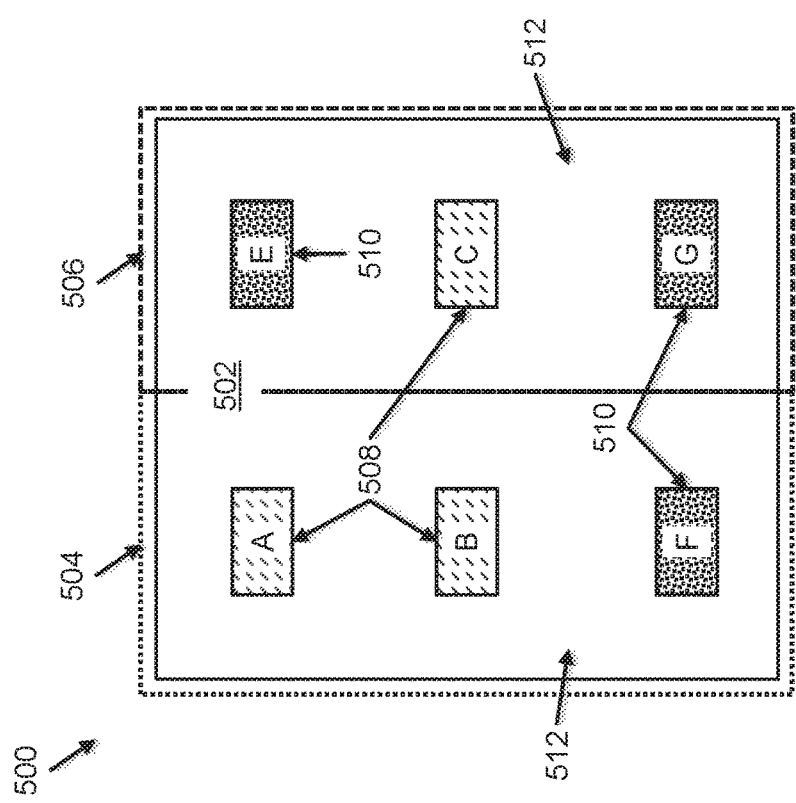
FIG. 5A depicts a cross-sectional view of an embodiment of a substrate patterned by an electron-emission patterning head by a maskless patterning method.

FIG. 5A depicts a top-down view of part of a pattern of functionalization of a microfluidic device 500. Microfluidic device 500 may have a top surface 502 divided into a first region 504 and a second region 506. First region 504 and second region 506 may have a same perimeter shape and a same-sized area within the perimeters thereof, and adjoin each other along one side. First region 504 and second region have different functionalization patterns located within the region perimeters. Description of the process of functionalizing the regions 504 and 506 may be illustrative of the performance of micro plasma functionalization in general on substrates. First region 504 and second region 506 contain a first set of areas 508, having a first type of functionalization, and a second set of areas 510, having a second type of functionalization thereon. First region and second region 506 may be functionalized with the first and second sets of areas without a masking process being performed to protect part of the top surface 502 from double processing or destruction of a previously-functionalized area during a current functionalization step. Top surface 502 may also contain an area 502 that has a third type of functionalization that differs from both the first type and second type of functionalization found in the first and second sets of areas. In an embodiment, the third type of functionalization may be an original type of surface functionalization present on a top surface of a substrate prior to any surface functionalization by spatially selective plasma processing.

FIGS. 5B-5E depict patterns 520, 530, 540, and 550 of spatially-selective surface functionalization that may be performed in order to generate a surface functionalization pattern depicted in microfluidic device 500, described previously. For purposes of convenience in describing surface functionalization, the patterns depicted herein share a common pattern perimeter 526. However, in many embodiments, a pattern perimeter may have different dimensions during a process of performing surface functionalization, according to a dimension of a pattern portion, and according to an ability of the patterning head to modify a shape and dimension of a distribution of electron beams and/or micro plasmas during surface functionalization. FIG. 5B depicts first pattern 520, having an activated portion 524 and a deactivated portion 522 within a pattern perimeter 526. Activated portion 524 includes two activated spaces within pattern perimeter 526. FIG. 7C depicts second pattern 530, having within pattern perimeter 526, deactivated space 532 and activated space 534. Deactivated portion 534 includes a single activated space. FIG. 5D depicts, within pattern perimeter 526, activated portion 544 and deactivated portion 542, and FIG. 5E depicts, within pattern perimeter 526, activated portion 554 and deactivated portion 552. Activated portion 554 includes two activated spaces.

In a representative, but non-limiting embodiment of a method of forming the surface functionalization pattern depicted in microfluidic device 500, the patterns depicted in FIGS. 5B-5E may be applied in any order. In an embodiment, functionalization patterns may be formed on a substrate top surface sequentially in a single region (such as region 504), before moving patterning head above second region 506 for a second set of surface functionalization steps [e.g., patterns 520 and 540 may be applied during functionalization of first region 504, prior to functionalization of second region 506 using patterns 530 and 550]. In an embodiment, functionalization patterns may be formed in different regions according to functionalization types, wherein, e.g. first set of areas 508 may be functionalized before any areas of second set of areas are functionalized on top surface 502 [e.g., patterns 520 and 530 may be applied to the first and second regions, completing functionalization of first set of areas 508, before patterns 540 and 550 are applied to the first and second regions, completing functionalization of the second set of areas 510]. Because micro plasmas formed by the patterning head may be regulated to remain separate within the working volume between a patterning head and a substrate top surface, spatial separation of functionalized areas and micro plasmas may allow maskless plasma functionalization of top surface without harm to previously functionalized areas. Determination of an order of micro plasma patterning of a substrate top surface may relate to a desired speed of functionalization of a top surface, a complexity of a functionalization pattern, a resolution of a micro plasma produced in the working volume, and other factors associated with compatible chemistry in the plasma, consumption of reactive species by the plasma during surface functionalization, accuracy of positioning the patterning head with respect to features on the substrate top surface, and a speed of refreshing or purging a working volume when changing from one type of functionalization chemistry to a different type of surface functionalization chemistry.

Figure 6:
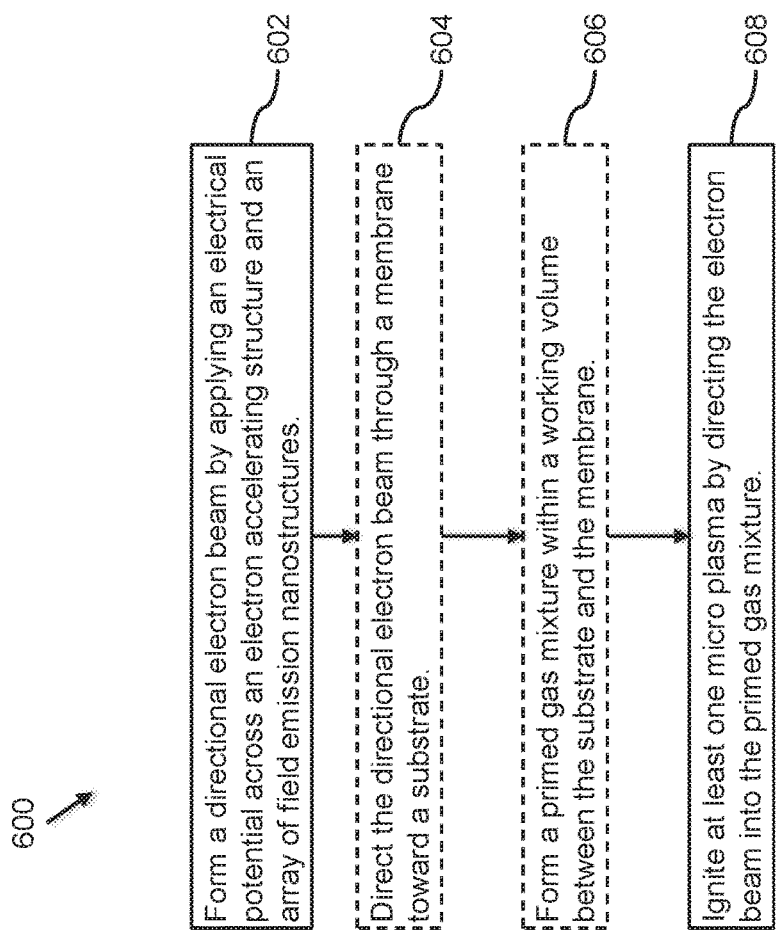
FIG. 6 depicts a flow diagram of an implementation of a method of generating a patterned array of micro-plasmas.

FIG. 6 depicts a flow diagram of an implementation of a method 600 of generating a patterned array of microplasmas. In a first operation 602, at least one directional electron beam may be formed by applying a potential difference between an accelerating structure and an array of electron emission structures of an electron source. A number of electron beams formed upon application of the potential difference to the accelerating structure and the array of emission structures may be a function of a number of individual emission structures, or loci of the array of emission structures, in the electron source. A number and pattern of emission structures, or loci, may be adjusted during operation of a patterning head by an instruction received from a control element of a plasma device, where the control element stores a pattern of surface functionalization, processes the pattern, sends information regarding the pattern to an instruction generator to determine an order of operations to form the pattern on a substrate surface, and regulates the distribution (or pattern) of micro plasmas that form a pattern by activating or deactivating individual emission structures, or loci of an array of emission structures, in the patterning device.

In an optional operation 604, the directed electron beam may be directed through a membrane having a first membrane face and a second membrane face toward a substrate. A membrane may be configured to permit creation of a pressure differential between an interior of a sealed enclosure and the exterior of the sealed enclosure. A membrane may be selectively permeable to gases, or may have a pinhole located therein to allow some gas to enter the interior portion of a sealed enclosure while the interior portion is being pumped to a reduced pressure. An interior portion of a sealed enclosure may have a pressure as low as $10^{-9}$ Torr while an exterior portion (outside the sealed enclosure) may have a pressure of about 760 Torr. The velocity, or energy, of the directed electron beam, may be regulated by adjusting the potential difference between emission structures and the electron accelerating structure of the electron source. By regulating the electron beam energy, a plasma device may regulate plasma density, the species that are formed in the micro plasmas in the plasma, and (optionally) the impact velocity of the ionized species against the substrate surface during surface functionalization.

Figure 7:
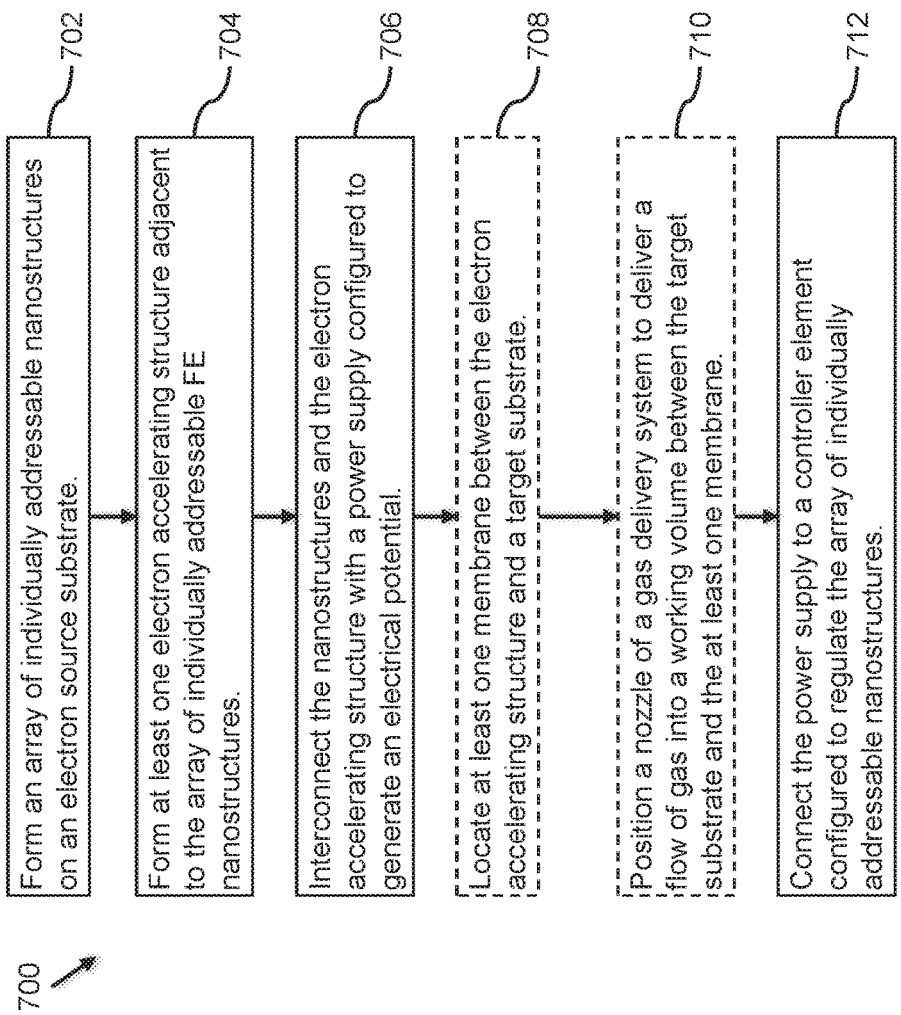
FIG. 7 depicts a flow diagram of an implementation of a method for modifying surface functionalization of a material.

In an optional operation 606, the working volume between the patterning device and the substrate may be primed with a gas mixture supplied via nozzles of the patterning head to adjust the chemistry of the plasma during surface functionalization. The chemistry may be adjusted according to a type of functionalization desired in a particular part of the surface functionalization process. In an operation 608, at least one micro plasma is ignited by directing the at least one directional electron beam FIG. 7 depicts a flow diagram of an implementation of a method 700 for making a spatially selective surface functionalization device, or plasma device. In an operation 702, an array of individually addressable electron emission structures, or loci in an array of clusters of electron emission structures, may be formed on an electron source substrate. Electron emission structures may be thermionic emission structures, field emission (FE) nanostructures or pyroelectric (PE) nanostructures located on conductive pads of an electron source substrate, the conductive pads being connected to a power supply and configured to apply a negative voltage to the emission structures during operation of a plasma device.

In an operation 704, an electron accelerating structure may be formed in a patterning head in close proximity to an electron source substrate. A ratio of a lateral dimension of the electron accelerating structure and a distance between the electron accelerating structure and an electron source substrate may range from between about 5:1 to about 10:1, although other, larger ratios, may be possible.

In an operation 706, electron emission structures of the electron source substrate, and the electron accelerating structure, may be interconnected at a power supply configured to generate an electrical potential between the electron source substrate and the electron accelerating structure. In an embodiment, an electron source substrate may be held at a voltage between about −1 kV and about −10 kV, while an electron accelerating structure may be held at a positive voltage ranging between about +1 kV and about +10 kV.

In an operation 708, a membrane may be located in a wall of a sealed enclosure to allow passage of directed beams of electrons from the nanostructures of the electron source substrate to the working volume outside the sealed enclosure. A membrane may be a single film membrane, or may have bilayers configured to allow passage of electrons out of the sealed enclosure.

In an operation 710, a gas delivery system nozzle may be positioned to deliver a flow of gas into a working volume of a plasma device. The working volume may be located between the membrane and the surface of a target substrate being functionalized by the plasma device. A working volume may have a gas flow delivery rate configured to refresh plasma reactant species during surface functionalization. A gas delivery system may include gaseous species and liquid species that may be aerosolized or evaporated by a carrier gas in order to prime a gas mixture in the working volume. In an operation 712, a controller element may be connected to the plasma device to regulate activation and deactivation of the nanostructures during surface functionalization.

In various embodiments, the chip includes a substrate formed from one or more of silicon, silicon dioxide, quartz, or silicon, preferably silicon. The individually addressable electron emission structures of the emission structure array may be a combination of one or more of the following: nano rods, nanowires made of a conductive or semiconductor material (such conductive or semiconductor materials including, but not limited to silicon, silicon carbide, and carbon), as well as carbon nanotubes and fullerene-like structures, tunneling cold field emitter cathodes, and pyroelectric material cathodes. Individually addressable nanostructures may be grown directly on a substrate material, or may be deposited onto a substrate material, or regions of a substrate material that are electrically connected to a power supply for the electron source of the patterning head.

In some embodiments, the techniques described herein may be used to form an analytical chip like that described in a U.S. Patent Application titled SELF-FLOWING MICROFLUIDIC ANALYTICAL CHIP filed on the same day as this patent filing, the contents of which are incorporated by reference. In some embodiments, the analytical chip may be analyzed with a pump-free microfluidic analytical system described in a U.S. Patent Application tiled STAND ALONE MICROFLUIDIC ANALYTICAL CHIP DEVICE, filed on the same day as the present patent filing, the contents of which are incorporated by reference.

What is claimed is:

1. A method of modifying a surface with a plasma, the method comprising:

energizing a first set of individually addressable electron emission structures in an electron source, the electron source having a membrane with a first surface and a second surface, the first set comprising a plurality of individually addressable electron emission structures;

creating a blend of gases in a working volume adjacent to the second surface of the membrane, the second surface being on an outer surface of the electron source;

accelerating electrons from the first set of individually addressable electron emission structures towards the membrane;

forming a first set of micro plasmas where the accelerated electrons from the first set of individually addressable electron emission structures intersects the blend of gases;

adjusting a distance between a substrate and the second surface such that the first set of micro plasmas intersects a surface of the substrate at a first location: and energizing a second set of individually addressable electron emission structures in the electron source to form a second set of micro plasmas that intersect the surface of the substrate at a second location, wherein:

the first set of micro plasmas has a first distribution of intersection points with the surface of the substrate, the second set of micro plasmas has a second distribution of intersection points with the surface of the substrate, the second distribution is different from the first distribution, and during forming the second set of micro plasmas, functionalization of the surface of the substrate at the first distribution of intersection points with the surface of the substrate remains unchanged within an overlap area of the surface of the substrate, the first distribution of intersection points having a first perimeter on the surface of the substrate, the second distribution of intersection points having a second perimeter on the surface of the substrate, and the overlap area overlapping the first perimeter and the second perimeter.

2. The method of claim 1 further comprising modifying a set of functional groups on the surface of the substrate at the first distribution of intersection points or the second distribution of intersection points, and wherein the surface outside the first and the second distributions of intersection points does not undergo modifying a set of functional groups during formation of the first set of micro plasmas or the second set of micro plasmas.

3. The method of claim 1, further comprising modifying the first distribution of intersection points into the second distribution of intersection points while the first set of micro plasmas intersects the surface of the substrate, upon displacement of the substrate beneath the electron source.

4. The method of claim 1, further comprising forming:

the first distribution of micro plasmas at a first position on the surface of the substrate according to a first instruction, the forming of the first distribution of micro plasmas being by the first set of micro plasmas, and the second distribution of micro plasmas at a second position on the surface of the substrate according to a second instruction, wherein:

the first instruction is different from the second instruction;

the first distribution is different from the second distribution;

the first position is different from the second position; and the second distribution of micro plasmas corresponds to a second portion of a pattern, the second portion being different from a first portion corresponding to the first distribution of micro plasmas.

5. The method of claim 4, wherein both the first and the second distributions of micro plasmas is formed by an array of electron emission structures of the electron source, at least part of the first and the second distributions of micro plasmas being formed by the same electron emission structures of the electron source.

6. The method of claim 5, wherein at least a first electron emission structure at a first location of the array and at least a second electron emission structure at a second location of the array are configured to be activated independently.

7. The method of claim 1, further comprising vacuuming to form a pressure differential across the membrane, wherein the working volume contains the gas mixture at a first pressure and an interior of the electron source has a second pressure smaller than the first pressure.

8. The method of claim 6, further comprising activating an electron emission structure configured to receive at least one instruction and to activate or deactivate electron emission structures at locations in the array according to the at least one instruction.

9. The method of claim 1, wherein both the first and the second sets of electron emission structures comprise pyroelectric electron (PE) emission structures.

10. The method of claim 1, further comprising a plurality of individually addressable thermal elements configured to undergo thermal changes to generate a residual electrical charge on individual pyroelectric nanostructures.

11. The method of claim 10, wherein the individually addressable thermal elements comprise:

a plurality of micro heating elements; and a plurality of micro cooling elements.

12. The method of claim 9, wherein the PE emission structures further comprise a plurality of electron accelerating structure configured to trigger departure of electrons from PE emission structures.

13. A method of modifying a surface with a plasma, the method comprising:

energizing a first set of individually addressable electron emission structures in an electron source, the electron source having a membrane with a first surface and a second surface, the first set comprising a plurality of individually addressable electron emission structures;

creating a blend of gases in a working volume adjacent to the second surface of the membrane, the second surface being on an outer surface of the electron source;

accelerating electrons from the first set of individually addressable electron emission structures towards the membrane;

forming a first set of micro plasmas where the accelerated electrons from the first set of individually addressable electron emission structures intersects the blend of gases; and adjusting a distance between a substrate and the second surface such that the first set of micro plasmas intersects a surface of the substrate at a first location, wherein:

a first distribution of micro plasmas is formed at a first position on the surface of the substrate by the first set of micro plasmas according to a first instruction, a second distribution of micro plasmas is formed at a second position on the surface of the substrate according to a second instruction, the first instruction is different from the second instruction, the first distribution is different from the second distribution, the first position is different from the second position, and the second distribution of micro plasmas corresponds to a second portion of a pattern, the second portion being different from a first portion corresponding to the first distribution of micro plasmas.

14. The method of claim 13, further comprising vacuuming to form a pressure differential across the membrane, wherein the working volume contains the gas mixture at a first pressure and an interior of the electron source has a second pressure smaller than the first pressure.

15. The method of claim 13, further comprising activating an electron emission structure in an array of electron emission structures in the electron source, the electron source being configured to receive at least one instruction and to activate or deactivate electron emission structures at locations in the array according to at least one instruction.

16. The method of claim 13, further comprising selectively addressing a plurality of individually addressable thermal elements configured to undergo thermal changes to generate a residual electrical charge on individual pyroelectric nanostructures.

17. A method of modifying a surface with a plasma, the method comprising:
energizing a set of individually addressable electron emission structures in an electron source, the electron source having a membrane with a first surface and a second surface, the set comprising a plurality of individually addressable electron emission structures;
creating a blend of gases in a working volume adjacent to the second surface of the membrane, the second surface being on an outer surface of the electron source;
accelerating electrons from the set of individually addressable electron emission structures towards the membrane;
vacuuming to form a pressure differential across the membrane, wherein the working volume contains the gas mixture at a first pressure and an interior of the electron source has a second pressure smaller than the first pressure;
forming a set of micro plasmas where the accelerated electrons from the set of individually addressable electron emission structures intersects the blend of gases; and
adjusting a distance between a substrate and the second surface such that the set of micro plasmas intersects a surface of the substrate at a first location.

18. The method of claim 17, further activating an electron emission structure in an array of electron emission structures in the electron source, the electron source being configured to receive at least one instruction and to activate or deactivate electron emission structures at locations in the array according to at least one instruction.

19. The method of claim 17, wherein the set of electron emission structures comprises pyroelectric electron (PE) emission structures.

20. The method of claim 17, further comprising selectively addressing a plurality of individually addressable thermal elements configured to undergo thermal changes to generate a residual electrical charge on individual pyroelectric nanostructures.

21. A method of modifying a surface with a plasma, the method comprising:
energizing a set of individually addressable electron emission structures in an electron source, the electron source having a membrane with a first surface and a second surface, the set comprising a plurality of individually addressable electron emission structures;
creating a blend of gases in a working volume adjacent to the second surface of the membrane, the second surface being on an outer surface of the electron source;
accelerating electrons from the set of individually addressable electron emission structures towards the membrane;
forming a set of micro plasmas where the accelerated electrons from the set of individually addressable electron emission structures intersects the blend of gases; and
adjusting a distance between a substrate and the second surface such that the set of micro plasmas intersects a surface of the substrate at a first location, wherein the electron emission structures comprise pyroelectric electron (PE) emission structures.

* * * * *